United States Patent [19]

Batz et al.

[11] 4,415,700

[45] Nov. 15, 1983

[54] HYDROPHILIC LATEX PARTICLES AND USE THEREOF

[75] Inventors: Hans-Georg Batz, Tutzing; Paul Tanswell, Planegg; Manfred Baier, Pöcking-Possenhofen, all of Fed. Rep. of Germany; Karel Boúchal; Jaroslav Kálal, both of Prague; František Švec, Hřebeč; Eva Žůrková, Prague, all of Czechoslovakia

[73] Assignees: Boehringer Mannheim GmbH, Mannheim-Waldhof, Fed. Rep. of Germany; Tschechoslowakische Academie der Wissenschaften, Prague, Czechoslovakia

[21] Appl. No.: 331,114

[22] Filed: Dec. 16, 1981

[30] Foreign Application Priority Data

Dec. 23, 1980 [CS] Czechoslovakia ............... 9235-80
Dec. 23, 1980 [DE] Fed. Rep. of Germany ....... 3048883

[51] Int. Cl.[3] .................. C08L 33/00; C08L 37/00; C08F 20/32; G01N 33/54
[52] U.S. Cl. ........................ 524/548; 424/3; 523/335; 523/410; 524/801; 524/811; 436/533
[58] Field of Search ................ 424/3, 12; 524/548, 524/801, 811; 523/335, 410

[56] References Cited

U.S. PATENT DOCUMENTS

| | | | |
|---|---|---|---|
| 3,223,670 | 12/1965 | Cantor et al. | 523/410 |
| 3,440,199 | 4/1969 | Lindemann et al. | 523/410 |
| 4,056,496 | 11/1977 | Mancini et al. | 523/410 |
| 4,089,828 | 5/1978 | Vasishth et al. | 523/410 |
| 4,133,383 | 2/1979 | Rembaum et al. | 524/809 |

*Primary Examiner*—Ronald W. Griffin
*Attorney, Agent, or Firm*—Felfe & Lynch

[57] ABSTRACT

Hydrophilic latex particles consisting of a homo- or co-polymer of monomers which are sparingly soluble in water, which hydrophilic latex particles can be prepared by emulsion polymerization in the presence of a water-soluble, radical-forming initiator but without an addition of an emulsifier, stabilizer or wetting agent. A process for the preparation of these hydrophilic latex particles, wherein a monomer which is sparingly soluble in water or several monomers which are sparingly soluble in water are dispersed in water and, with the exclusion of oxygen, for example in an inert atmosphere, are homo- or co-polymerized by emulsion polymerization in the presence of a water-soluble, radical-forming initiator but without any addition of an emulsifier, stabilizer or wetting agent.

A diagnostic agent containing these hydrophilic latex particles as carrier and biologically and/or immunologically active substances covalently bound to this carrier either directly or via a coupling agent as a bridge.

30 Claims, No Drawings

HYDROPHILIC LATEX PARTICLES AND USE THEREOF

This invention relates to hydrophilic latex particles and a process for their preparation. In additional aspect the invention relates to the use of such particles as carrier materials for biological and/or immunologically active substances in diagnostic agents.

For the agglutination of antigen-antibody complexes, which is utilised in immunology for many diagnostic determinations because it can be carried out especially quickly and simply and frequently can be observed with the naked eye, use has been made for a long time of hydrophobic latex particles as carriers for immunologically active substances, for example for antibodies. These hydrophobic latex particles usually consist of polystyrene homo- and co-polymers, for example styrene-butadiene co-polymers or acrylonitrile-butadiene-styrene co-polymers (ABS), which are prepared by emulsion polymerisation.

In general, in the case of the long-known emulsion polymerisation, four components are present: a monomer which is sparingly soluble in water or a mixture of various monomers which are sparingly soluble in water, water, an emulsifier and a water-soluble initiator. The monomer is thereby emulsified by the emulsifier in the form of fine droplets, whereby, due to the coming together of several emulisifier molecules inter alia comparatively large micelles are formed, some of which are empty and some of which are filled with monomer molecules, the latter being referred to as "solubilisation" of the monomer. The water-soluble initiator forms radicals which can initiate or activate the polymerisation not only of individual monomer molecules in the aqueous phase but also in the micelles filled with monomer molecules as well as in the monomer droplets. However, polymerisation takes place preponderantly in the swollen micelles since, on the one hand, the monomer concentration in the micelles is substantially greater than in the proximity of individual dissolved monomer molecules and, on the other hand, the probability of activation of micelles is considerably greater because of their substantially greater number in comparison with the number of monomer droplets. The diameter of the filled micelles increases during the polymerisation until finally they are converted into spheroidal latex particles. The emulsifier molecules of the non-activated micelles and those from the surface of the consumed monomer droplets cover the surface of the latex particles and thus contribute to the stabilisation of the resulting polymer dispersion.

These latices prepared according to the known process, with the addition of an emulsifier or of an emulsion stabiliser, which can be, for example, a tenside or wetting agent, have the following disadvantages which, in particular, impair their use as carriers for immunologically-active substances and prevent their use in continuous solution measurement systems:

1. on the hydrophobic surface of the latex particles, a plurality of other serum components is bound non-specifically, in addition to the desired immunologically-active substances, for example antibodies;

2. the immunologically-active substances which are only bound adsorptively but not covalently can again be dissolved off during the measurement in the course of a diagnostic test;

3. the tensides used in the emulsion polymerisation as emulsifier or stabiliser can destroy the structure and thus the activity of biologically-active proteins because they diffuse into the aqueous solution;

4. in the case of removal of the stabilising tensides, the latex suspension coagulates and the stabilisation is also destroyed in the case of centrifuging. The precipitate hereby resulting can only be resuspended with difficulty or cannot be resuspended at all in the previous state.

In order to avoid these disadvantages, various proposals have already been made which, however, are only able to solve some of the above-mentioned problems:

Thus, Federal Republic of Germany Patent Specification No. 2,203,377 describes latex particles with a particle size of 0.01 to 0.9 $\mu$m. made from carboxylated ABS co-polymer and carboxylated styrene-butadiene co-polymers, which latex particles can be used as serologically inert carriers for biologically-active proteins, the proteins thereby being covalently bound to the carrier via the carboxyl groups introduced into the latex, with the formation of amide bonds.

Federal Republic of Germany Patent Specification No. 2,812,845 describes hydrophobic latices with a particle size of 0.05 to 1 $\mu$m. made from ABS co-polymers in which the latex is also modified with carboxyl groups and is condensed with a reactive side chain so that immunologically-active substances can also be co-valently bound.

These known hydrophobic latices admittedly overcome the above-mentioned second problem but all the other disadvantages remain unchanged.

Consequently, an attempt has also been made to use hydrophilic gels as carriers for immunologically-active substances, instead of hydrophobic latices. Since hydrophilic gels have no or only a very small adsorption property but, on the other hand, the covalent bonding of proteins on to such gels is known, "microgels" have been suggested which, on the basis of their manner of preparation and of their particle diameter, can equally well be called "latices". Such hydrophilic latices are known, for example, from U.S. Pat. No. 4,138,383. They consist of spheroidal particles with a diameter of less than 0.35 $\mu$m. which are prepared under the conditions of an aqueous emulsion polymerisation initiated by free radicals, the monomers used thereby being acrylamides, acrylic acid, methacrylic acid or acrylates. The emulsifiers used can be, for example, metal soaps. Biologically- and/or immunologically-active substances are bound to the so obtained hydrophilic microgels in known manner via carbodiimide or glutardialdehyde bridges. In this manner, the first two of the four above-mentioned problems are admittedly solved but not the third or fourth problems since the emulsion polymerisation must, as before, be carried out with the addition of an emulsifier or stabiliser.

One object of the present invention is to provide hydrophilic latex particles, a process for the preparation thereof and a diagnostic agent containing these with which it is possible to avoid all four of the above-mentioned disadvantages. Thus, in particular, it is an object of the present invention to provide hydrophilic latex particles which are able co-valently to bind biologically and/or immunologically-active substances which do not impair the structure and thus the activity of the biologically-active proteins, the stabilisation of which is not destroyed by centrifuging and which coagulate and can subsequently easily be resuspended again.

Thus, according to the present invention, there are provided hydrophilic latex particles consisting of a homo- or co-polymer of monomers which are sparingly soluble in water, which hydrophilic latex particles can be prepared by emulsion polymerisation in the presence of a water-soluble, radical-forming initiator but without any addition of an emulsifier, stabiliser or wetting agent.

According to a preferred embodiment of the present invention, at least a part of the monomers from which the hydrophilic latex particles are made consists of an epoxide containing at least one polymerisable carbon-carbon double bond in the molecule.

Surprisingly, we have found, contrary to the opinion which has long prevailed in expert circles, which is also mentioned in the above-cited prior art, that the addition of an emulsifier, stabiliser or of a wetting agent is not necessary for carrying out the emulsion polymerisation. The removal of emulsifier residues from the polymeric latex particles, which is usually difficult and laborious and which has hitherto absolutely necessary because the metal soaps or tensides used as emulsifiers diffuse out of the latex particles and impair or completely destroy the biological activity of the proteins covalently bound on to the latex particles, is no longer necessary.

The use of glycidyl compounds containing at least one polymerisable double bond as monomer has proved to be especially advantageous. In these compounds, the polymerisable double bond is hydrophobic and the epoxy group, the oxirane ring, is hydrophilic. The latex suspensions resulting according to the present invention do not coagulate in spite of the absence of any emulsifier, stabiliser or wetting agent. The stabilising of the latex suspension is also not destroyed by centrifuging. Since the terminal epoxide group is very readily available for various reactions (hydrolysis, ammonolysis, aminolysis, condensations), the epoxide groups must so cover the surface of the monodisperse distributed latex spheroids that they are outwardly oriented in the aqueous phase.

According to the present invention, the monomers used are preferably glycidyl methacrylate, glycidyl acrylate, glycidyl vinyl ether, glycidyl vinyl phthalate and 3,4-epoxybut-1-ene. One of these monomers can be used exclusively so that the resultant hydrophilic latex particles is a homopolymer but a mixture of these monomers can also be co-polymerised.

For controlling the content of epoxide groups, one or more of the mentioned glycidyl compounds can also be co-polymerised with, for example, styrene, dienes, acrylamides, methacrylamides, alkyl, hydroxyalkyl and aminoalkyl acrylates, alkyl, hydroxyalkyl and aminoalkyl methacrylates, vinyl ethers, vinyl esters, N-vinyl-pyrrolidone and the like.

Polymerisation can also be carried out in the presence of monomeric, polymerisable derivatives of dyestuffs or fluorescing compounds, for example fluorescein, coloured or fluorescing latex particles thereby being obtained which can be used for the detection of antigens or antibodies in human and animal tissues. These methods of detection are especially useful for the preparation of tissue sections in histology. As monomeric polymerisable derivatives, it is preferable to use dyestuffs or fluorescing compounds into which methacrylic or acrylic radicals have been incorporated in known manner.

In order to increase the sparing solubility of the resultant latex particles, conventional crosslinking agents can be added during the emulsion polymerisation, for example alkylene or hydroxyalkylene diacrylates, alkylene or hydroxyalkylene dimethacrylates, alkylene-bisacrylamides or alkylene-bis-methacrylamides, divinylbenzene or the like.

The initiator used can be any water-soluble initiator conventionally employed for emulsion polymerisation; according to the present invention it is preferable to use persulphates, perborates, hydrogen peroxide or appropriate redox systems.

The process according to the present invention of emulsifier-free emulsion polymerisation of one or more monomers which are sparingly soluble in water for the preparation of latex particles is very sensitive towards atmospheric oxygen or free oxygen. Therefore, the oxygen must be carefully removed from all of the polymerisation components and vessels by thorough boiling, by distillation under inert gas atmosphere or by passing in nitrogen, argon or some other inert gas.

According to the present invention, the emulsifier-free emulsion polymerisation is preferably carried out with a bath ratio, referred to the volume, between the aqueous and monomer phase of 8:1 to 16:1.

The concentration of the initiator dissolved in the aqueous phase is preferably from 0.5 to 1.5 g./liter and the concentration of the epoxide in the monomer phase is preferably 1 to 100% by weight.

The emulsion polymerisation is preferably carried out at a temperature of from 0° to 80° C. The temperature used is dependent upon the selected initiator; in the case of using potassium persulphate, it is preferable to operate at a temperature of 60° to 70° C. The period of reaction, which is also dependent upon the choice of initiator, is from 5 to 40 hours.

The hydrophilic latex particles according to the present invention are strictly spheroidal and monodisperse, the particles being of substantially equal size with a diameter of from about 0.15 to 1.5 $\mu$m.

At the end of the emulsion polymerisation, the hydrophilic latex particles may still contain residues of non-polymerised monomers which can be removed by steam distillation or dialysis. Here, too, the especially advantageous properties of the hydrophilic latex particles according to the present invention are also manifest in the latex particles can be sedimented by centrifuging without the stabilisation being destroyed so that they can subsequently be redispersed agin. In this way, the latex according to the present invention can be purified in a simple manner by repeated centrifuging and decanting.

The terminal free epoxide groups of the latex according to the present invention are highly reactive with regard to the most varied chemical substances and can, therefore, easily be hydrolysed, oxidised with periodiates or periodic acid to aldehyde groups, reacted with ammonia, primary amines, diamines or hydrazines to give primary or secondary amino groups or modified with the help of other known reactions. In spite of the absence of an emulsifier, the emulsion of the latex according to the present invention has such a high stability that the modification of the epoxide groups can, if desired, also be carried out during the emulsion polymerisation so that the polymerisation reaction gives a latex, the surface of which is modified, for example, with primary amino groups. The modified or derivatised epoxide groups are thus available for the "coupling" with biologically and/or immunologically active proteins which are thus covalently bound on to the hydrophilic latex particles functioning as a carrier.

The initially mentioned problem is thus further solved by the use of the hydrophilic latex particles according to the present invention as serologically inert carriers for biologically and/or immunologically active substances, for example as carriers for peptides, proteins, enzymes, hormones, vitamins, antigens, antibodies and micro-organisms.

Thus, the present invention also provides a diagnostic agent containing hydrophilic latex particles according to the present invention as carrier and biologically and/or immunologically active substances of the above-mentioned kind covalently bound to this carrier directly or via a coupling agent as a "bridge".

The diagnostic agents according to the present invention are especially useful for use in radioimmuno (RIA), enzyme immuno (EIA) and so-called ELISA (enzyme-linked immunosorbent assay) tests.

The following Examples are given for the purpose of illustrating the present invention:

EXAMPLE 1

0.08 g. Potassium persulphate ($K_2S_2O_8$) is dissolved in 80 ml. distilled water and freed from atmospheric oxygen by passing through nitrogen for 30 minutes. Simultaneously, 10 ml. glycidyl methacrylate are freed of atmospheric oxygen in the same way. Both components are introduced into a glass reactor and treated with nitrogen for a further 10 minutes. Thereafter, the reactor is closed and the reaction is carried out with continuous stirring for 6 hours at a temperature of 65° C. After this time, the conversion is 98%. The reaction product is a latex of spheroidal, monodisperse distributed polyglycidyl methacrylate particles with a diameter of 0.44 μm.

EXAMPLE 2

In the manner described in Example 1, 160 ml. distilled water, in which 0.08 g. potassium persulphate is dissolved, and 10 ml. of a mixture of 15% by weight of glycidyl methacrylate and 85% by weight of styrene are individually freed from oxygen and then reacted together for 6 hours, with continuous stirring, at a temperature of 65° C. Thereafter, the conversion is 71.6%. The non-polymerised residual monomers are removed by steam distillation. The resultant monodisperse co-polymeric latex particles have a diameter of 0.22 μm.

EXAMPLE 3

In the manner described in Example 1, a solution of 0.1 g. potassium persulphate in 100 ml. distilled water and 10 ml. of a mixture of 15% by weight of glycidyl methacrylate and 85% by weight of vinyl acetate are reacted together. The conversion is 80%. The residual monomers are removed by steam distillation. The resultant latex consists of monodisperse, spheroidal particles with a diameter of 0.16 μm.

100 ml. of the so prepared latex are mixed with 100 ml. of a 0.1 M sodium hydroxide solution and left to stand at a temperature of about 25° C. for 24 hours. The stability of the latex is also maintained during and after the hydrolysis. The emulsion is centrifuged, the supernatant is poured off and the solid phase is again redispersed in water. Centrifuging and redispersing are repeated twice. The resultant neutral emulsion is adjusted to a pH value of 3 with 1 M sulphuric acid and mixed with periodic acid in an amount equivalent to the epoxide groups. Oxidation is carried out at 25° C. for about 24 hours. Subsequently, the unreacted, low molecular weight materials are removed by dialysis. The modified latex particles of the stable emulsion contain 2.8% by weight or 0.97 mMol/g. of aldehyde groups.

EXAMPLE 4

In the manner described in Example 1, a solution of 0.1 g. potassium persulphate in 100 ml. distilled water and 10 ml. of a mixture of 15% by weight of glycidyl methacrylate and 85% by weight isoprene are reacted at a temperature of 65° C. for 24 hours. The conversion is 76%. The residual monomers are subsequently removed by steam distillation, stable monodisperse distributed spheroidal latex particles with a diameter of 0.25 μm. thereby being obtained.

100 ml. of this emulsion are subsequently mixed with 100 ml. of 25% aqueous ammonia solution and left to stand for 24 hours at ambient temperature, the epoxide groups thereby being converted by ammonolysis into amino groups. The reaction product is subsequently treated with periodic acid, a latex thereby being obtained which contains 4.5% by weight of 1.55 mMol/g. of aldehyde groups.

EXAMPLE 5

In the manner described in Example 1, a solution of 1.5 g. potassium persulphate in 1.5 liters of water and 15 ml. glycidyl methacrylate are individually freed from oxygen and reacted together. A further 120 ml. of oxygen-free glycidyl methacrylate are continuously added dropwise into the reaction vessel in the course of 6 hours, with the exclusion of oxygen. Thereafter, polymerisation is continued for 30 minutes. The conversion is then 85% and the resultant particles have a diameter of 1.1 μm.

EXAMPLE 6

In the manner described in Example 1, 10 ml. of a mixture of 1% by weight glycidyl methacrylate and 99% by weight styrene and a solution of 0.1 g. potassium persulphate in 100 ml. distilled water are polymerised at 65° C. for 22 hours, hydrophilic latex particles thereby being formed with a diameter of 0.5 μm. The conversion is 90%.

EXAMPLE 7

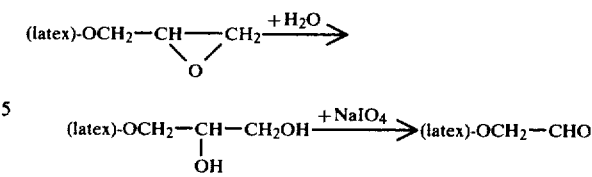

20 ml. of a latex suspension prepared according to Example 1 are stirred overnight with 5 ml. of 2 N sodium hydroxide solution at ambient temperature and then dialysed against water for 5 hours. The remaining suspension is adjusted to pH 3 by the addition of 100 mg. sodium periodate and stirred overnight at ambient temperature and then dialysed for 4 hours against distilled water.

EXAMPLE 8

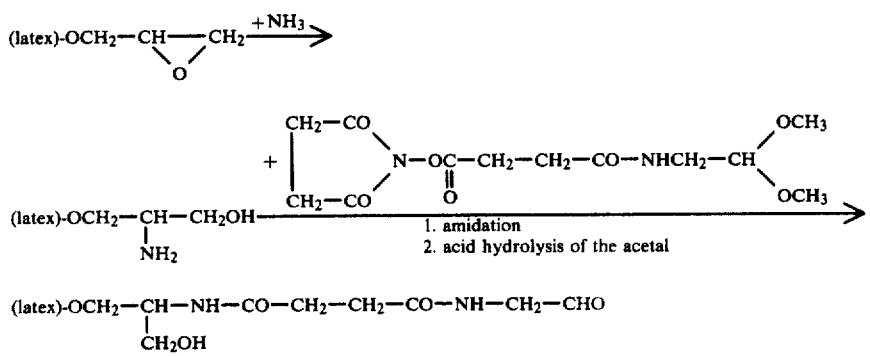

20 ml. of a latex suspension prepared according to Example 1 are stirred with 10 ml. concentrated ammonia solution for 20 hours and then dialysed for 48 hours against running water. The suspension obtained is centrifuged off. Thereafter, the nitrogen content of the dry substance is about 1%, which corresponds to an amination of about every tenth epoxide unit but, in the case of a preferred reaction on the surface, certainly corresponds to a higher degree of derivatisation. The centrifuged off solid substance is again taken up in 20 ml. of 0.1 N aqueous sodium hydroxide solution. 1.5 g. Succinic acid hydroxysuccinimide ester amidoacetaldehyde acetal, dissolved in 6 ml. dimethylformamide, is added dropwise thereto, while stirring. The resultant suspension is further stirred for 3 hours, thereafter adjusted to pH 3 with 1 N hydrochloric acid and then dialysed against running distilled water for 12 hours.

EXAMPLE 9

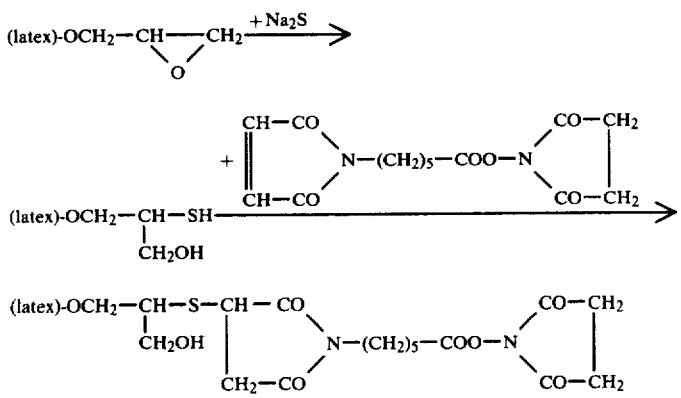

20 ml. of a latex suspension prepared according to Example 1 are mixed with 0.5 g. sodium sulphide nonahydrate and stirred for 2 days at ambient temperature. The reaction mixture is subsequently dialysed against running distilled water until the suspension is odourless and the suspension is then centrifuged off. The dry substance contains about 2% of sulphur, which corresponds to a derivatisation of about every tenth epoxide unit but in the case of a preferred reaction on the surface, certainly corresponds to a higher degree of derivatisation.

The centrifuged off product is mixed with 1 g. 6-maleinimidohexanoic acid hydroxysuccinimide ester, dissolved in 6 ml. dimethylformamide, stirred for 3 hours at ambient temperature and then dialysed for 12 hours against running distilled water.

EXAMPLE 10

Formation of latex-gamma-globulin conjugates 1 ml. amounts of gamma-globulin solution (containing 56.6 mg. of protein) are mixed, in each case, with 20 ml. of a latex suspension
 (a) prepared according to Example 1,
 (b) according to Example 7,
 (c) according to Example 8 and
 (d) derivatised according to Example 9
and dialysed for 12 hours at ambient temperature. The remaining suspensions are centrifuged off. Subsequently, free protein is determined in the supernatant. From the values found, there can be calculated the proportion bound on to the latex particles:

batch a: 8 mg. gamma-globulin, bound
batch b: 43 mg. gamma-globulin, bound
batch c: 15 mg. gamma-globulin, bound
batch d: 19 mg. gamma-globulin, bound.

EXAMPLE 11

Formation of latex IgG conjugates

As described in Example 10, from an IgG solution and various latex suspensions, there are prepared latex-IgG conjugates. The loading of the latex particles with IgG molecules is determined by antibody complex formation.

In the following, there are described two diagnostic agents as examples of the use of the hydrophilic latex particles according to the present invention, namely, for the immunological determination of thyroxine ($T_4$) with the help of $T_4$-antibodies from anti-$T_4$-serum from sheep and for the determination of human thyr(e)otropin (TSH) in serum with the help of the double antibody separation technique.

EXAMPLE 12

Use of homopolyglycidyl methacrylate latex particles as carrier of anti-T$_4$-serum from sheep; diagnostic agent for carrying out a T$_4$-ELISA For determining thyroxine (T$_4$) by means of ELISA, T$_4$-antibodies from an anti-T$_4$-serum from sheep are first covalently bound on to the hydrophilic homoglycidyl methacrylate latex particles according to the present invention, the latter being derivatised according to one of Examples 7 to 9 and reacted with the T$_4$-antibodies analogously to Examples 10 and 11. The so obtained solid face antibodies represent the first reagent for the test. As the second reagent, T$_4$ is marked in known manner with an enzyme suitable for this purpose, for example peroxidase (POD) or β-galactosidase (β-Gal), i.e. "coupled" to give an enzyme conjugate. In the present Example, β-Gal is used as the enzyme. The third reagent is the sample having an unknown content of T$_4$ and the fourth reagent is a conventional substrate for the β-Gal of the enzyme conjugate which, in the present case, is nitrophenyl-β-galactoside in tris-hydrochloric acid buffer (pH 7.3).

The test principle depends upon the following three reactions:

1. The immunological reaction between the T$_4$-antibodies covalently bound on to the hydrophilic latex particles, on the one hand, and the enzyme-marked T$_4$ ("enzyme conjugate") and the free T$_4$ contained in the sample, on the other hand. In this reaction, a competitive binding thus takes place between the solid face antibodies, the enzyme conjugate and the T$_4$ of the sample.

2. The bound/free (B/F) separation, i.e. a separation of bound and free enzyme conjugate. This separation can advantageously be carried out by centrifuging or by dialysis, for example against water or an appropriate buffer solution.

3. The enzyme detection reaction which takes place between the enzyme conjugate and the substrate usually employed and specific for the enzyme used and can be monitored colorimetrically or in some other known manner. The enzyme activity determination can take place either in the centrifugate (free portion) or in the resuspended precipitate (bound portion).

Carrying out of the Experiment

The latex-anti-T$_4$ suspension prepared in the above-described manner is diluted in water or buffer solution in the ratio of 1:1000. 0.5 ml. amounts of this suspension are mixed with 100 μl. amounts of T$_4$-serum standard solutions with various known T$_4$ contents and 100 μl. amounts of a T$_4$-β-Gal conjugate solution. The reaction mixtures are incubated for 30 minutes at ambient temperature. During the incubation, one batch is continuously shaken whereas a second bath with the same T$_4$ standard content is merely left to stand. Thereafter, each of the suspensions is centrifuged and the supernatant in which the free phase is present is separated off. The bound phase, i.e. the T$_4$-β-Gal conjugate bound to the solid face antibodies, is present in the precipitate. For the determination of the enzyme activity, this is mixed with an excess of a substrate solution consisting of 450 mg./l. p-nitrophenyl-β-galactoside (Sigma)
100 mM sodium chloride
10 mM magnesium chloride
10 mM tris buffer/HCl
0.4% (v/v) mercaptoethanol (pH value 7.3) and the extinction measured in known manner at a wavelength of 405 nm. It is found that the latex particles held in suspension without external mechanical mixing give a signal reduced by about 11%.

After T$_4$ calibration curves have been obtained in this manner, determinations are subsequently carried out in the same manner in which, instead of 100 μl. T$_4$ standard serum, there are, in each case, used 100 μl. of samples of unknown T$_4$ content and the extinction of the bound phase measured after resuspension in substrate solution.

It was found that the hydrophilic latex particles are outstandingly suitable as carriers for antibodies and also for antigens and do not impair their immune activity. Therefore, they can be used with great advantage as carriers in solid face enzyme immune tests. Furthermore, it was found that the hydrophilic latex particles in buffer media remain suspended for a long time, which means that the density of the particles is approximately equal to one. In addition, the hydrophilic latex particles according to the present invention can readily be centrifuged and resuspended without loss of immune reactivity.

EXAMPLE 13

Enzyme immune assay (EIA) for the determination of human thyreotropin (TSH)

The determination of TSH in human serum is of considerable importance for the diagnosis of diseases of the thyroid. A primary hypothyreosis can be recognised by a considerably increased basal TSH concentration (10 to 100 μU TSH/ml.). Furthermore, a hyperthyreosis can be excluded with certainty when the TSH basal value in the serum does not increase from 0.5 to 3 μU/ml. after stimulation with TRH (thyroid-releasing hormone). If, on the other hand, the TSH value increases by at least 2.5 μU/ml. but not by more than 25 μU/ml., then the thyroid metabolism is, with great probability, not disturbed. An increase of more than 25 μU/ml. from a more or less slightly increased basal value is indicative of a latent preclinical hypothyreosis. Enzyme immune assays for TSH are already known (see Clinica Chemica Acta, 67, 263–268/1976; Enzyme labelled immunoassay of hormones and drugs, published by S. B. Pal. Walter de Gruyter, Berlin and New York, 1978, pp. 327–337; Analytical Biochemistry, 96, 419–425/1979). However, these known methods of determination require excessively long periods of incubation (up to 5 days), are insensitive (5 μU TSH/ml.) or require the use of expensive measurement apparatus (fluorometer or luminometer), a device for mixing the batches also being necessary.

The use of the hydrophilic latex particles according to the present invention now makes possible a photometric determination of the TSH with a total incubation time of only 2.5 days according to the double antibody technique. The second antibody is thereby covalently bound on to hydrophilic latex particles according to the present invention. The bound enzyme activity is then measured after a B/F separation. Since the latex particles have a density which is not substantially greater than that of water, they also remain in suspension during the enzyme reaction, the usual mixing thereby being unnecessary. In the case of the use of very dilute latex suspensions, which, because of the high loadability with antibodies, is certainly possible, the centrifuging of the particles after the enzyme reaction has taken place is also unnecessary since the suspension can be measured photometrically.

In contradistinction to the latices usually employed in immunological test processes, the antibody-loaded, hydrophilic polyglycidyl methacrylate particles according to the present invention can easily be resuspended after centrifuging. For the same reason, a very low non-specific adsorption of the enzyme-marked antigen (bound activity in the absence of primary antibodies) is shown.

Carrying out of the Experiment 0.2 ml. TSH standard (international reference preparation MRC 68/38 in TSH-free serum) is incubated with 0.1 ml. of a 1:150,000 dilution in water or appropriate buffer solution of a known anti-TSH antiserum, for example from guinea pigs. After 12 hours, 0.1 ml. of a solution of an enzyme conjugate, consisting of TSH covalently coupled to glucose oxidase (GOD) (corresponding to about $1.5 \times 10^{-9}$ g. TSH), is pipetted into the mixture of the first stage. After a further 12 hours, 0.1 ml. of a latex suspension are pipetted into this mixture. The suspension contains 0.1 to 1 mg./ml. of methacrylate latex, whereby, as described in Example 11, per 1000 mg. of the dry latex particles, there are added 5 to 150 mg. of protein of an immune globulin fraction which has been obtained from a goat antiserum against guinea pig IgG and thus are covalently bound on to the hydrophilic latex particles. After one hour, centrifuging is carried out and the precipitate of the latex particles is washed with 1 ml. of an appropriate buffer solution, the latex particles thereby being resuspended. Subsequently, centrifuging and washing are again carried out several times. The supernatants are discarded.

To each batch there is pipetted 1 ml. of a substrate solution for GOD and briefly shaken. Thereafter, the latex particles remain uniformly suspended for at least 2 hours. The suspension is then transferred to a measurement cuvette and the extinction measured at 405 nm. From each extinction there is deducted a substrate blank value $L_1$. $L_1$ is the extinction of 1 ml. of substrate solution which contains the same mass of loaded latex particles as the above-mentioned latex suspension which was added to the mixture of anti-TSH antiserum and TSH-GOD.

The so determined extinctions are plotted for various standard concentrations of TSH. With the help of the calibration curves thus obtained, there are read off the concentrations of TSH in clinical samples of unknown content on the basis of the determined extinctions.

As appropriate buffer solution, there is preferably used a 0.04 M phosphate solution (pH 7.4) which contains 0.005 M ethylenediamine-tetraacetic acid and 0.1% bovine serum albumin, as well as 0.15 M sodium chloride.

As GOD substrate solution, it is preferred to use an aqueous solution which contains 5 g./100 ml. glucose, 100 mg./100 ml. 2,2'-azino-di-[3-ethylbenzthiazolone-6-sulphonic acid] (ABTS), 5 mg./100 ml. peroxidase (POD) and 0.05 M phosphate buffer (pH 5.6).

For comparison, the TSH contents of three serum samples were determined not only with the above-described EIA(A) but also with the help of a double antibody-RIA (B). As the following Table shows, there is a good agreement between the values obtained by both methods:

|  | A | B |
|---|---|---|
| serum 1 | 11.2 μU/ml. | 12.5 μU/ml. |
| serum 2 | 7.3 μU/ml. | 7.1 μU/ml. |
| serum 3 | 3.8 μU/ml. | 4.5 μU/ml. |

From the above-described TSH determinations, too, it can be seen that the hydrophilic latex particles according to the present invention are outstandingly useful as carriers for biologically and/or immunologically active substances and especially for antibodies.

Determination of the Non-specific Bonding

A TSH standard sample is treated in the manner described above under "carrying out of the experiment" (sample C) and compared with a further sample of the same kind (sample D) which has been subjected to almost the same reactions as sample C, merely the anti-TSH antiserum being omitted. Comparison of the extinctions measured on the two samples C and D in the suspension show that the non-specific binding amounts to less than 1.5%:

|  | sample C | sample D |
|---|---|---|
| extinction measured in the sample minus $L_1$ | 1.028 | 0.015 |

It will be understood that the specification and examples are illustrative but not limitative of the present invention and that other embodiments within the spirit and scope of the invention will suggest themselves to those skilled in the art.

What is claimed is:

1. Hydrophilic latex particles which are sparingly soluble in water consisting of a homo- or co-polymer of monomers containing at least one epoxy group and at least one polymerizable carbon-carbon double bond in the molecule.

2. Hydrophilic latex particles as claimed in claim 1, prepared by emulsion polymerization in the presence of a water soluble, radical-forming initiator and in the absence of an emulsifier, stabilizer or wetting agent.

3. Hydrophilic latex particles as claimed in claim 2, wherein the particles consist of a homo-polymer comprising at least 10% epoxide in the molecule.

4. Hydrophilic latex particles as claimed in claim 2, wherein the particles consist of a co-polymer wherein one of the monomers comprising at least 10% of the co-polymer, is an epoxide containing at least one polymerizable carbon-carbon double bond in the molecule.

5. Hydrophilic latex particles as claimed in claim 2, wherein at least one of the monomers is an epoxyalkylene compound.

6. Hydrophilic latex particles as claimed in claim 2, wherein at least one of the monomers is a glycidyl ester or glycidyl ether.

7. Hydrophilic latex particles as claimed in claim 6, wherein said ester is glycidyl acrylate or glycidyl methacrylate.

8. Hydrophilic latex particles as claimed in claim 2, wherein the homo- or co-polymer is cross-linked with a di- or polyunsaturated cross-linking agent.

9. Hydrophilic latex particles as claimed in claim 2, wherein the particles are monodisperse spheroids, all having substantially the same diameter in the range of from 0.15 to 1.5 μm.

10. Hydrophilic latex particles as claimed in claim 2, wherein the homo- or co-polymer has terminal hydroxyl, primary or secondary amino, thiol, aldehyde or carboxyl groups.

11. Hydrophilic latex particles as claimed in claim 2, also containing co-polymerized dyestuffs or fluorescing compounds.

12. Hydrophobic latex particles as claimed in claim 1 comprising 15% to 100% of said monomers containing epoxy groups.

13. Process for the preparation of hydrophilic latex particles as claimed in claim 1, which process comprises dispersing at least one monomer which is sparingly water soluble in water and, under the exclusion of oxygen, polymerizing same by emulsion polymerization in the presence of a water soluble radical forming initiator and in the absence of an emulsifier, stabilizer, or wetting agent.

14. Process as claimed in claim 13, wherein the polymerization is carried out in an inert atmosphere.

15. Process as claimed in claim 13, wherein an epoxide containing at least one (co)polymerizable carbon-carbon double bond in the molecule is dispersed in water alone or in admixture with other co-polymerizable monomers, and is homo- or co-polymerized by emulsion polymerization without the addition of an emulsifier.

16. Process as claimed in claim 15, wherein an epoxyalkylene compound or a glycidyl ester or glycidyl ether is used as the epoxide.

17. Process as claimed in claim 15, wherein glycidyl acrylate or glycidyl methacrylate is used as the epoxide.

18. Process as claimed in claim 13, wherein the emulsion polymerization is carried out with the addition of a di- or poly-unsaturated cross-linking agent.

19. Process as claimed in claim 13, wherein the emulsion polymerization is carried out with a bath ratio (water:monomer phase) of 8:1 to 16:1, referred to the volumes.

20. Process as claimed in claim 13, wherein the initiator concentration in the aqueous phase is 0.5 to 1.5 g./liter.

21. Process as claimed in claim 13, wherein the concentration of epoxide in the monomer phase is 1 to 100% by weight.

22. Process as claimed in claim 13, wherein the emulsion polymerization is carried out at a temperature of from 0° to 80° C.

23. Process as claimed in claim 13, wherein a latex containing terminal epoxide groups is, during or after the emulsion polymerization, subjected to hydrolysis, ammonolysis, aminolysis or thiolysis with aqueous alkali metal hydroxide solution, aqueous ammonia solution, with a primary amine, a hydrazine or a sulfide, terminal hydroxyl, amino groups, mono- or disubstituted amino groups or thiol groups thereby being formed.

24. The process of claim 23 further comprising subsequently reacting said groups, enzymatically, with periodate, or with periodic acid, to convert them into aldehyde groups.

25. Diagnostic agent containing hydrophilic latex particles as claimed in claim 1 as a carrier and also comprising biologically or immunologically active substance covalently bound to said particles.

26. Diagnostic agent as claimed in claim 25, wherein said covalent bonding to the carrier is via a coupling agent.

27. Diagnostic agent as claimed in claim 25, wherein said covalent bonding to the carrier is via direct coupling.

28. Diagnostic agent as claimed in claim 25, wherein the biologically and/or immunologically active substances are selected from peptides, proteins, enzymes, hormones, vitamins, antigens, antibodies and microorganisms.

29. Diagnostic agents as claimed in claim 25 for the determination of thyroxine, containing a thyroxine antibody as said biologically or immunologically active substance.

30. Diagnostic agent as claimed in claim 25 for the determination of human thyreotropin, containing a human thyreotropin antibody as the biologically and/or immunologically active substance.

* * * * *